United States Patent [19]

Ochi et al.

[11] 4,300,556

[45] Nov. 17, 1981

[54] FACIAL BEAUTY DEVICE

[75] Inventors: Shuhei Ochi; Fumiya Ueda; Nobuyuki Morihara; Hiroshi Namba; Motohisa Nishino; Shigeo Yamamoto, all of Hikone, Japan

[73] Assignee: Matsushita Electric Works, Ltd., Osaka, Japan

[21] Appl. No.: 172,706

[22] Filed: Jul. 25, 1980

[30] Foreign Application Priority Data

Jul. 25, 1979 [JP] Japan .................................. 54/95258
Jan. 22, 1980 [JP] Japan .................................. 55/6217

[51] Int. Cl.[3] .................................................. A61F 7/00
[52] U.S. Cl. .......................................... 128/256; 128/368
[58] Field of Search ....................... 128/256, 368, 367; 4/160, 165

[56] References Cited

U.S. PATENT DOCUMENTS

| | | | |
|---|---|---|---|
| 3,511,236 | 5/1970 | Conlin et al. | 128/256 X |
| 3,707,971 | 1/1973 | Yamamoto | 128/368 |
| 3,768,483 | 10/1973 | Kosunoki | 128/368 |
| 4,190,052 | 2/1980 | McCarthy | 128/368 |

*Primary Examiner*—John D. Yasko
*Attorney, Agent, or Firm*—Burns, Doane, Swecker & Mathis

[57] ABSTRACT

A facial beauty device attainable, in addition to facial sauna effect with a heated and highly moistened atmosphere, a facial skin washing effect by means of water spray and simultaneously both facial skin tightening and massaging effects accompanying inherent cooling and spray pressure, respectively. The device is provided with a moistening means oscillating water in a reservoir within a body case at a frequency of an ultrasonic band and delivering generated mist into a hood on the case to provide a highly moistened atmosphere within the hood, means for heating the mist by passing it through an electric resistive heater or carrying it onto the hood with hot air stream heated by the heater, and means for spraying water in the reservoir or from a tank capable of automatically supplying water responsive to falling water level in the reservoir toward a face contacting opening of the hood through nozzles opened in the hood by means of a pump. Preferably further provided is a spray rocking mechanism for providing sprays of a pattern elongated in the width direction of the user's face and blown while being moved between jaw and forehead through nozzles positioned on the forehead side. As desired, the heating means is arranged so that only a hot air stream can be fed into the hood after water is sprayed.

18 Claims, 23 Drawing Figures

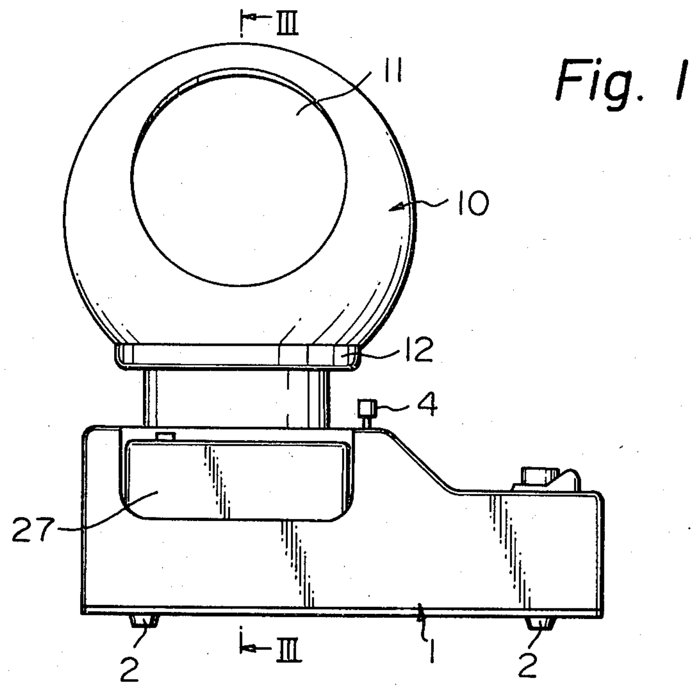
Fig. 1
Fig. 2
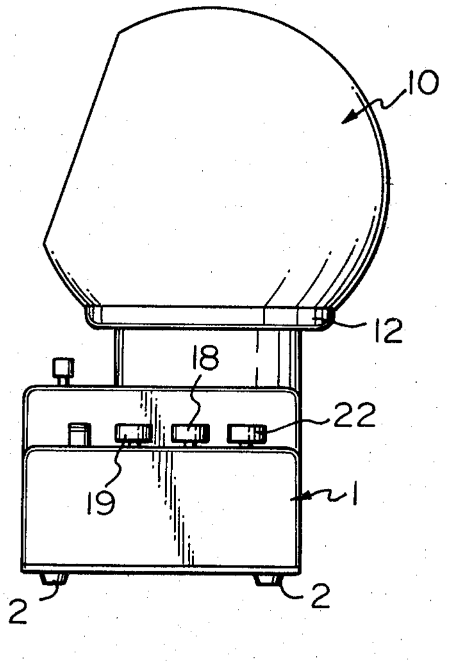

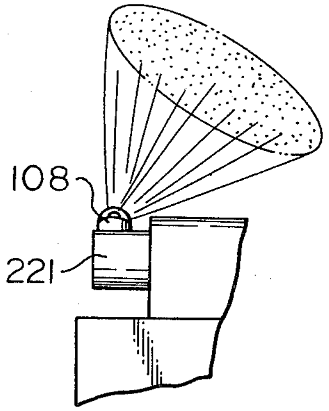
Fig. 10
Fig. 11A Fig. 11B Fig. 11C
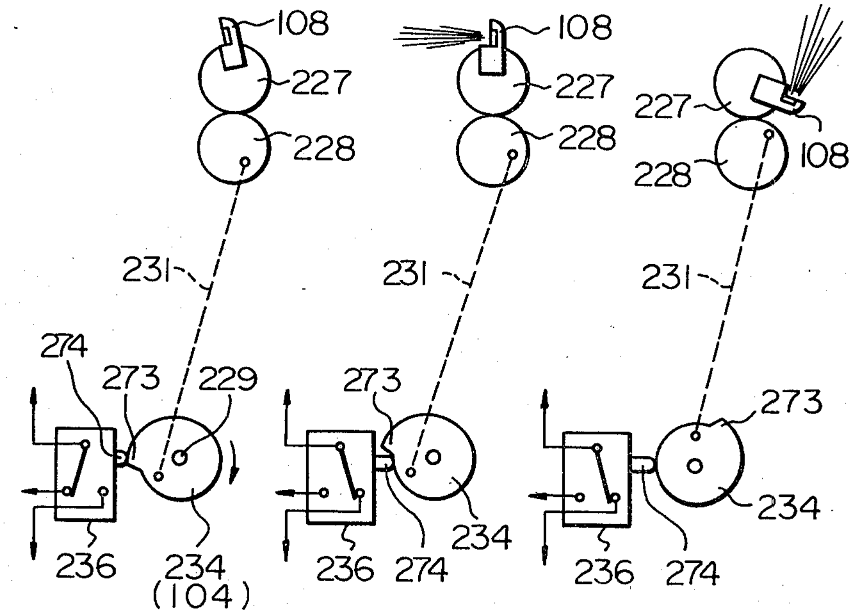

FACIAL BEAUTY DEVICE

The present invention relates to facial beauty devices generally known as "facial sauna" and, more particularly, to a face treatment equipment which can perform various treatments at least of warming, cooling and washing effects for face skin as well as a selective treatment of at least one of these effects.

In conventional facial beauty devices, a treatment has been made usually by applying to the user's face steam generated by an autoclave, alone or as combined with a facial beauty liquid having washing, nutritive and the like effects with respect to the facial skin, or with a steam ionizing device. Therefore, the facial beauty device of such type is intended mostly to have a so-called "sauna" effect of removing dusts, fats and time-lapsed cosmetic agents staying in skin pores by an expansion of the skin pores and a perspiration accompanying the warming. However, as these obstacles coming out of the skin pores only stay on the skin surface together with sweat and water drops deposited on the surface, the user must separate the face from the device and must wash the face with separately prepared warm or cool water or wipe the face surface with cloth or paper. Further, there is an inconvenience that the autoclave does not immediately generate steam and requires time until it generates steam sufficient for the "sauna" effect. Further, there is a danger that, as steam is jetted out while steam pressure within the autoclave is maintained, a clogging with any obstacle of the nozzle throttled to be of a small diameter easily causes the pressure within the autoclave to excessively rise and the autoclave to be exploded. Further, the "sauna" effect by the warming and eventual expansion of skin pores or the entire skin is effective to clean the skin as described above and to accelerate the metabolism in the skin structure. On the other hand, as a beauty treatment, it is desirable to again tighten the skin by cooling with water or the like after such warming but, in the conventional devices, such cooling can not be made. In the case of using the autoclave, further, the temperature of the steam to be used for the warming will be considerably so high when it is generated that it has been necessary to prevent any burning of the face and any unpleasantness at the time of use with such measures as a proper control of jetted-out amount of steam, reduction of the steam temperature or restriction of the steam pressure applied to the face by having the jetted steam reflected on the inside surface of a face resting hood provided on the device. The present invention has been suggested in view of these disadvantages in the conventional facial beauty devices.

A primary object of the present invention is, therefore, to provide a facial beauty device which is capable of not only warming the facial skin but also of cooling and washing the facial skin.

Another related object of the present invention is to provide a facial beauty device which can easily, conveniently and effectively perform various treatments necessary to elevate the facial beauty effect.

A further object of the present invention is to provide a facial beauty device which is made safe and easy to use by employing a means for warming the facial skin without involving no danger of explosion.

Another object of the present invention is to provide a facial beauty device which requires no special arrangement for maintaining safety at the time of practical use, eventually simple in the structure to lower the cost, and yet high in the facial beauty effects.

Still another object of the present invention is to provide a facial beauty device which can pleasantly perform respective warming, cooling, washing and the like treatments, without giving any unpleasant feeling to the user.

Yet another object of the present invention is to provide a facial beauty device which has a structure capable of performing respective warming, cooling, washing and the like treatments at the highest efficiency.

Still further object of the present invention is to provide a facial beauty device which has a structure capable of completely using up water stored within a reservoir for respective treatments of warming, cooling, washing and the like and is thus contributive to energy saving.

Further related object of the present invention is to provide a facial beauty device which has a structure capable of performing respective treatments for the facial beauty effect at a high efficiency and thus can be contributive to energy saving.

The present invention shall be described in detail in the followings with reference to certain preferred embodiments shown in accompanying drawings, in which:

FIGS. 1 to 3 show a facial beauty device of a first embodiment of the present invention, wherein FIG. 1 is a front elevation of the same, FIG. 2 is a side elevation of the same and FIG. 3 is a vertically sectioned side elevation taken along line III—III passing substantially through the center of a face resting hood of the same;

FIGS. 4 and 5 show a general structure of a facial beauty device of a second embodiment of the present invention, wherein FIG. 4 is a perspective view of the same and FIG. 5 is a vertically sectioned view substantially along the center line of the same;

FIGS. 9 and 10 are views for explaining spray patterns of respective nozzles of the water spraying means in the second embodiment, respectively in a plan view showing the movement of the spray pattern with the operation of the spraying means and an elevation of the spray pattern of one nozzle in one state.

FIGS. 11A to 11C are views for schematically explaining relations in the respective operating states of a switch cam, microswitch and nozzle in the water spraying means and its associated operating mechanism shown in FIG. 6;

FIGS. 13A and 13B are magnified views showing an example of structure and operation of the water spraying nozzle used in the second embodiment, wherein FIG. 13A is a vertically sectioned view of the same and FIG. 13B is a perspective view of the same;

FIGS. 14A and 14B show another embodiment of the water spraying nozzle used in the facial beauty device of the present invention, wherein FIG. 14A is a fragmentary vertically sectioned view of the same and FIG. 14B is a perspective view showing a spraying action of the same;

Figure 14A:
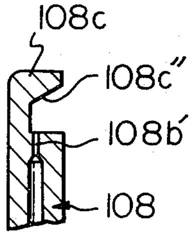
Figure 14B:
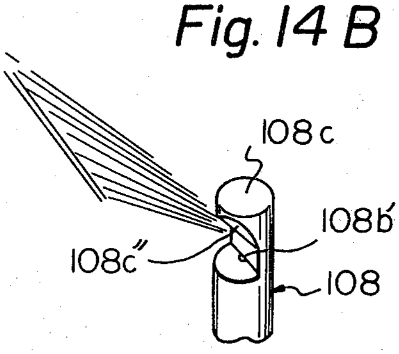
Figure 15A:
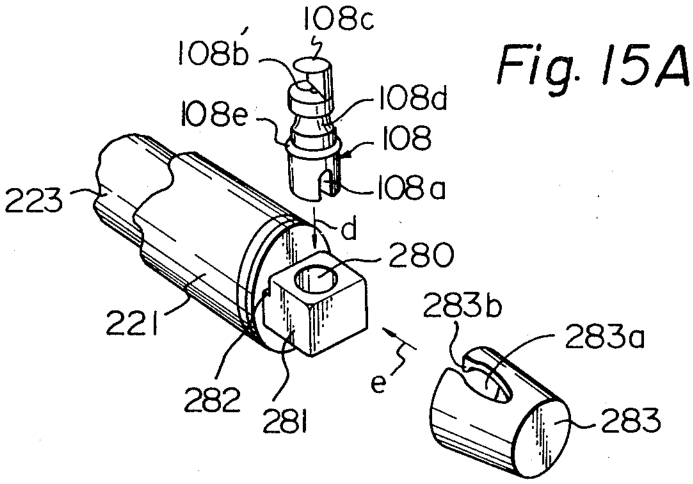
Figure 15B:
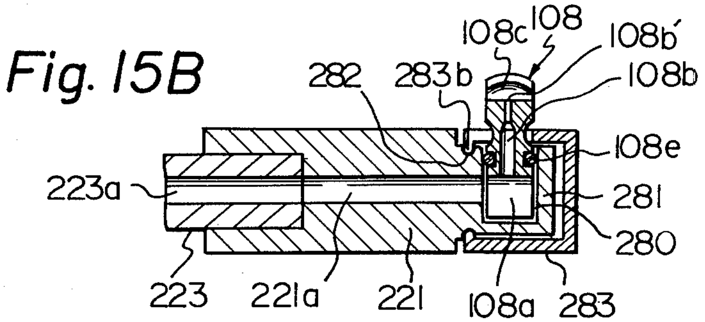
Figure 15C:
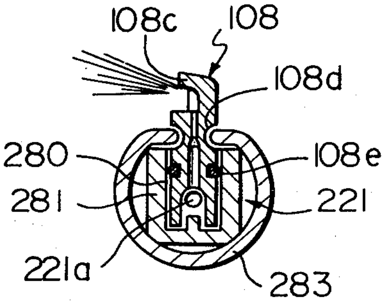
Figure 16:
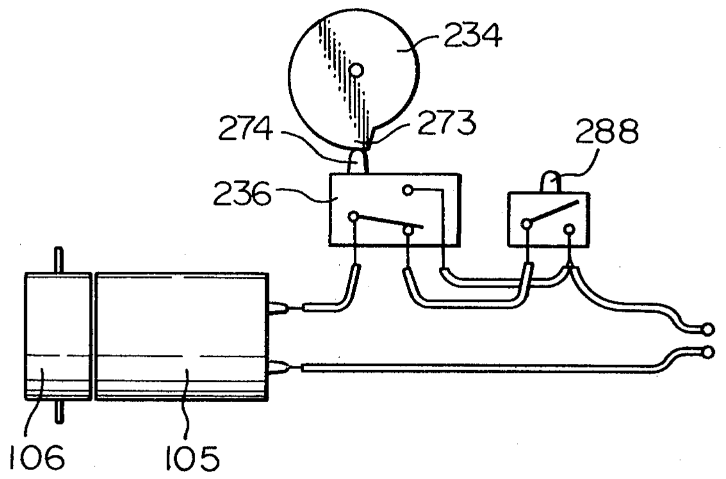
Figure 17:
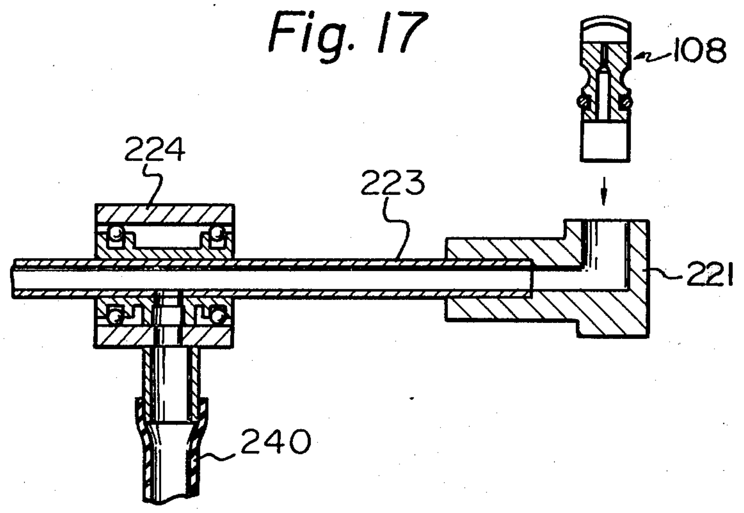
Figure 18:
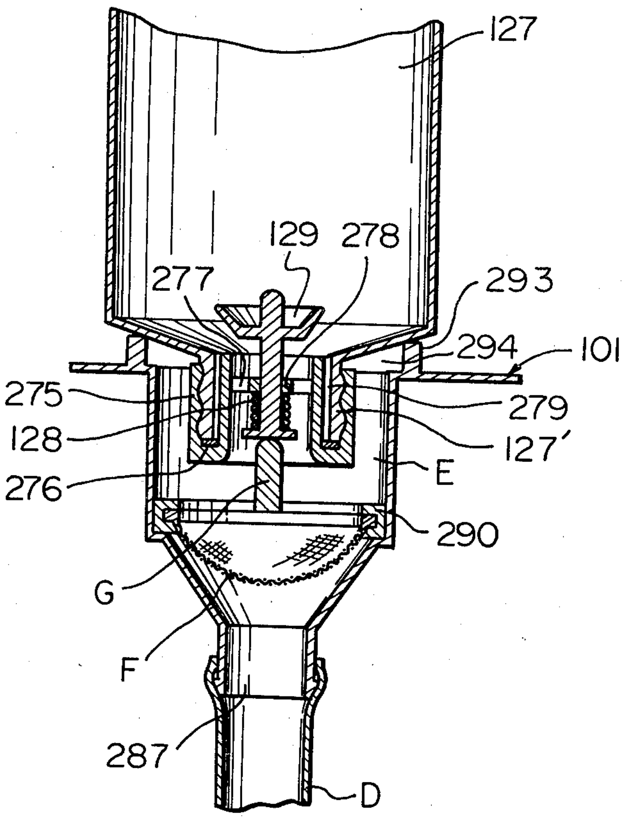

FIGS. 15A to 15C show a structure for fitting the water spraying nozzle shown in FIGS. 13 and 14 in the water spraying means of the facial beauty device of the second embodiment, wherein FIG. 15 is a fragmentary perspective view as disassembled of the same, FIG. 15B is a sectioned view in the lengthwise direction of the means as assembled of the same and FIG. 15C is a horizontally sectioned view of the nozzle part as assembled of the same;

FIG. 16 is a schematic circuit diagram showing operative relations between a switch cam for operating the water spraying means, a microswitch for normally driving a motor and pump of the water spraying means as operatively connected with the switch cam, and a push button switch specifically for draining water by driving the motor and pump in the second embodiment;

FIG. 17 is a partial sectioned view showing relation between a rockable pipe joint of the water spraying means and a connecting pipe rotatably fitting the nozzle and its holder to the joint in the second embodiment; and FIG. 18 is a fragmentary sectioned view as magnified showing detailed structure of a water feeding means used in the facial beauty device of the second embodiment.

While the present invention shall be detailed in the followings with reference to the illustrated embodiments, the intention is not to limit the present invention only to these embodiments shown but is to include all alterations, modifications and equivalent arrangements possible within the scope of appended claims.

Figure 3:
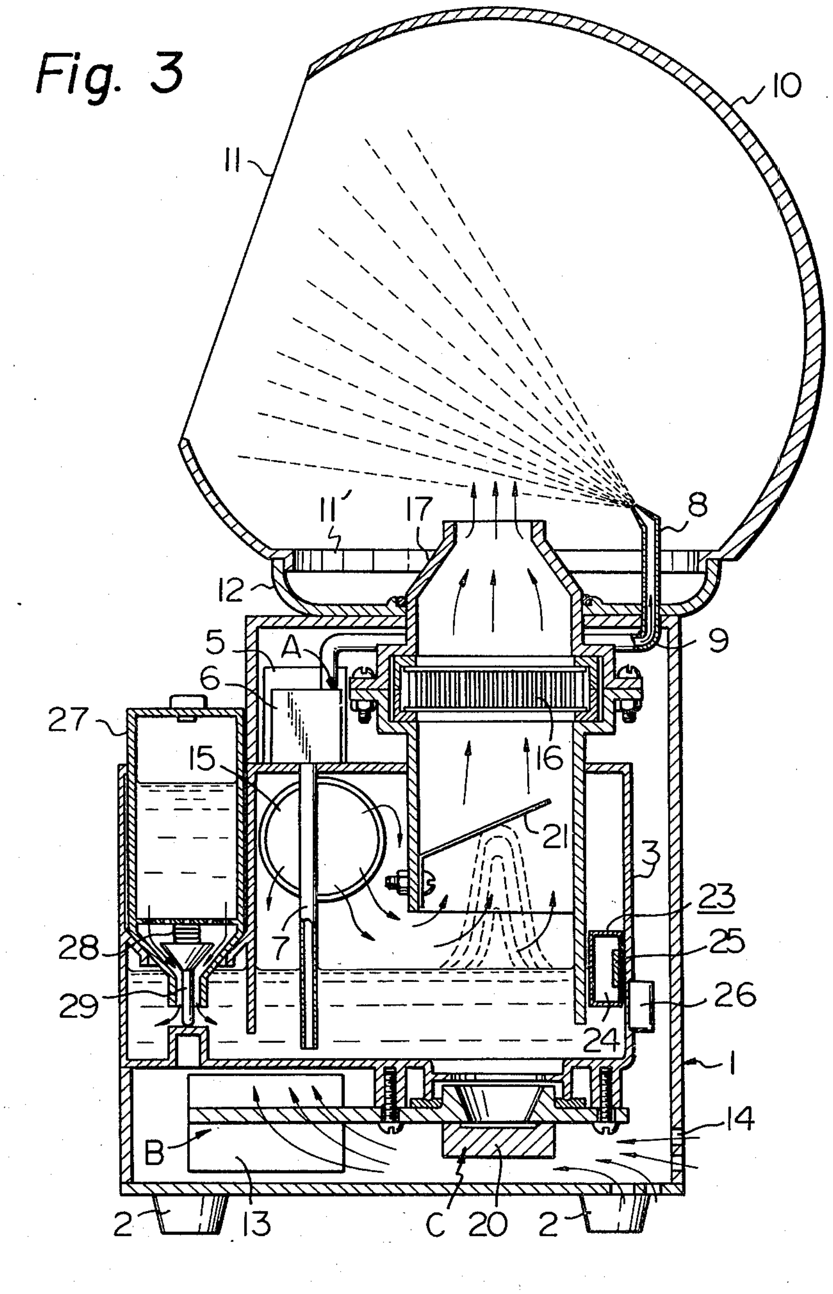

Referring first to the facial beauty device of the first embodiment according to the present invention with reference to FIGS. 1 to 3, this facial beauty device comprises generally a body case 1 containing respective means for later described various facial beauty treatments and having on the lower surface a plurality of feet 2 made of rubber for improving the stability of the entire device and a water reservoir 3 within it and a substantially spherical hood disposed on the upper surface of the case 1 for defining respective treatment atmospheres in front of the user's face rested against an opening 11 of the hood. Within the body case 1, there are arranged a water spraying means A for spraying water in the reservoir 3 into the hood 10, a heating means B for generating a heated air flow as directed into the hood 10 from the inside of the case 1 and a moistening means C for generating a mist of fine water droplets by oscillating water within the reservoir 3 at a frequency of ultrasonic band in the present instance. Switch knobs for the later described operations of these respective means are set on the case 1.

The water spraying means A comprises a water feeding pump 6 driven by a motor 5 switched on and off by operations of a knob of a water spraying switch 4 disposed on the upper part of the reservoir 3, a water suction pipe 7 connected at one end to a suction port of the pump and opened at the other end in the bottom of the reservoir 3 and a water delivery pipe 9 connected at one end to a delivery port of the pump 6 and formed at the other end to have a nozzle 8 positioned within the hood 10. The nozzle 8 in this case is made to spray water uniformly toward the entire area of the opening 11 of the hood 10.

Further, the hood 10 is formed, for example, of a synthetic resin to have, in addition to the opening 11, a lower opening 11' for receiving the nozzle 8 of the water spraying means and an open end of a later described delivery tube for the above described heated air flow and mist, whereas the lower opening 11' is covered by a receiving dish 12 between the periphery of the lower opening and the nozzle and delivery tube so that all water drops dropping from the inside space of the hood will be received by the dish 12 and drained thereout, and the dish 12 is adapted to hold thereon the hood 10 removably.

The heating means B comprises, in the illustrated case, a blowing device 13 arranged in the bottom of the case 1 and a heater 16 in the form of a porous plate made of, for example, a honeycomb-shaped positive characteristic electric resistive member which is held between a pair of electrode plates so as to extend in the cross-sectional direction of a delivery tube 17 substantially in the intermediate position of the tube 17 which communicates the upper space of the reservoir 3 with the inside space of the hood 10. The blowing device 13 sucks in the exterior air through a suction port 14 made through the outside wall in the lower part of the case 1 and generates an air stream flowing respectively through a ventilating port 15 opened in the upper part of the reservoir 3, the inside space of the reservoir 3 above water therein and the heater 16 and out of the open end of the delivery tube 17 into the hood 10. Therefore, the air stream flown through the heater 16 to which an electric current is being fed will be heated and will be blown as a hot wind into the hood. The heater 16 is provided with a heater adjusting switch 18 operated by a knob exposed on the case 1 so that the switching on and off of the heater as well as the amount of generated heat can be thereby adjusted. Also, the blowing device 13 is switched on and off to be adjusted in the volume of the blown wind by a wind volume adjusting switch 19 operated by a knob exposed also on the case 1 together with the switch 18. It will be here noticed that the reservoir 3 is adapted to reserve water only in a part at the bottom part and to leave the space in the upper part sufficient for allowing the air stream to pass therethrough.

Next, the moistening means c comprises generally an ultrasonic oscillator 20 provided in the bottom wall of the reservoir 3 with its ultrasound radiating port communicated with water within the reservoir 3 and, preferably, the ultrasound radiating port is positioned to be opposed to the lower opening of the delivery tube 17 connected to the upper part of the reservoir 3. Therefore, water in the reservoir 3 oscillated by the oscillator 20 will be jetted up as a mist of fine water droplets into the upper space of the reservoir, the thus generated mist is carried into the delivery tube 17 by the air stream due to the operation of the blowing device 13 of the heating means B to pass through the poronsplate heater 16 of the heating means B to be thereby heated and a mixed stream of the thus heated air and mist in the form of a hot steam is delivered into the hood 10 out of the upper end of the delivery tube 17. In this case, it is preferable that comparatively large water drops jetted up together with the mist and carried into the delivery tube 17 should not directly hit the heater 16 and, for this purpose, there is provided a shielding plate 21 across the delivery tube 17 but as inclined in the lengthwise direction while leaving on the periphery a clearance adapted to pass therethrough a sufficient amount of the mist of small droplets. The oscillator 20 is switched on and off by a mist generating and adjusting switch 22 operated by a knob provided in the upper part of the case together with the knobs of the switches 18 and 19 and its oscillating frequency is selectively varied so that the generated amount of the mist can be properly adjusted.

It is advantageous that, if the set position of the oscillator 20 in the bottom of the reservoir 3 is between the above described blowing device 13 and the exterior air suction port 14, the outer body of the oscillator is exposed to a suction air flow, so that the oscillator 20 will be cooled by the flow during the operation. Further, it is preferable to provide a means 23 for preventing the oscillator from being kept operated to be damaged when there is no water within the reservoir 3. For this purpose, the means 23 comprises a float 24 shiftable as operatively associated with the water level within the reservoir and having therein a permanent magnet 25 and a lead switch 26 positioned on the outer wall of the reservoir 3 close to the bottom thereof and in the shifting course of the float 24 as well as the magnet 25 so as to open and close an electrically operating circuit of the oscillator 20. Thus the lead switch 26 is operated to open the operating circuit by the magnet 25 of the float came down to a position opposing the switch 26 as the water level in the reservoir descends.

In order to keep the amount of the mist generated by the ultrasonic oscillator 20 to be constant at the respective selected operating frequencies of the oscillator 20, it is necessary to keep the water level within the reservoir 3 constant while the device is being used. For this purpose, it is preferable to employ a detachable water feeding tank 27 which is fitted to the case 1 and can automatically feed water into the reservoir 3 in response to the fall of the water level within the reservoir. A water delivery port provided at the lower end of this water feeding tank 27 is normally closed by a plug 29 which is biased into the closing position by a coil spring 28 and also by the water pressure of the water poured in the tank through a water feeding port provided at the upper end of the tank, so that the water will not leak out even when the tank is detached from the case 1 to be carried. When the water tank 27 with water therein is fitted to the body case 1, a projecting end of the plug 29 will contact the bottom surface of the reservoir 3 or, as in the present instance, a projection provided on the bottom surface with a height proper for determining a desired water level in the reservoir 3, the water feeding port will be opened against the pressing force of the spring 28 and the water pressure within the tank, then water is fed into the reservoir 3 and, when water fed into the reservoir reaches the desired level, the water feed will stop due to a pressure balance with the atmospheric pressure. When the water level in the reservoir 3 descends with the use of the spraying means A and moistening means C, the balance will be broken, water within the tank 27 will be again fed into the reservoir 3 and the desired water level will be maintained.

The operation of the above described first embodiment shall now be described. While in the present embodiment the respective spraying, heating and moistening means A to C can be separately operated by means of the different switches 18, 19 and 22, the most preferable example of the operation will be that the user operates the heating means B by operating the wind volume adjusting switch 19 to actuate the blowing device 13 and the heater adjusting switch 18 to actuate the heater 16, as well as the moistening means C by operating the mist generating and adjusting switch 22 so as to actuate the oscillator 20. Then, a moistened air flow of a volume and temperature optimum to a desired treatment generated in response to selected operating states of the respective switches is delivered into the hood from the open end of the delivery tube 17 and blown against the user's face rested against the hood opening 11. The skin structure of the user's face will be thus warmed, and moistened by the atmosphere of the heated and moistened air flow within the hood, the skin pores will be thereby opened, the metabolism in the face skin structure will be accelerated, and it becomes easy to drain old wastes and to remove obstacles staying within the skin pores to be a cause of the dirt of the face. Now, the user operates the switch 4 of the water spraying means A at this stage, then the water feeding pump 6 operates to suck up water from the reservoir 3 and jets it as a water spray out of the nozzle 8. As this water spray is blown against the face surface, the warmed face skin will be cooled while being washed and the skin structure accelerated in the metabolism while being expanded by once being warmed will be quickly tensioned. Needless to say, it is preferable to operate the water spraying means A after the skin is well warmed and moistened by the heating and moistening means B and C and to stop the operation of these means B and C while the face is being washed and cooled. Further, when the heating means B only is operated again after the face is washed and cooled, the face can be properly dried by a dry and heated air flow produced within the hood.

In the above described operation, the moistening means C is properly selectively operated by the operation of the switch 22 so that a selective amount of the mist will be generated from water within the reservoir 3 as oscillated by the ultrasonic oscillator 20 at a selected frequency and will be heated by the heater 16 together with the air stream caused by the heating means B, whereby a properly moistened high temperature atmosphere will be produced within the hood 10 and the face will be thereby warmed and moistened. Generally, when the water spraying means C is operated as described above after a sufficient performance of the warming action by this moistened atmosphere which is more favorable in the facial beauty effect than the warming only with a dry atmosphere, the face of which the metabolism has been accelerated and the old wastes and obstacles drained on the surface to be easy to flow together with the water drops of the moistened atmosphere deposited on the face can be very effectively washed and quickly cooled by the blown water sprays and the skin structure can be well tensioned. After this washing action is sufficiently made, only the heating means B is operated as described above, then the dry and heated air flow thereby produced will favorably dry the face, but in this case the heater adjusting switch 18 may be cut off so as not to heat the air flow with the heater 16, whereby the face surface can be dried with the air flow at the room temperature.

The temperature of the heated mist produced by the heating and moistening means is adjusted mostly by varying the amount of heat generated by the heater 16. However, this adjustment may be made also by varying the amount of the mist generated by the moistening means or the amount of the wind blown by the blowing device, so that the user can obtain the heated mist of a desired temperature, moistened degree and wind amount.

While the above described first embodiment comprises an arrangement of heated air stream generation as the heating means as well as a further arrangement of obtaining the moistened and heated air stream with a combination of the moistening means with the former arrangement, the face may be warmed directly by a radiant heat by such a heating means as a surface heater, infrared-ray heater or the like instead of the above combined arrangements, and such mist generating device as has been described above can be also used together with the heating by means of such radiant heat.

Figure 4:
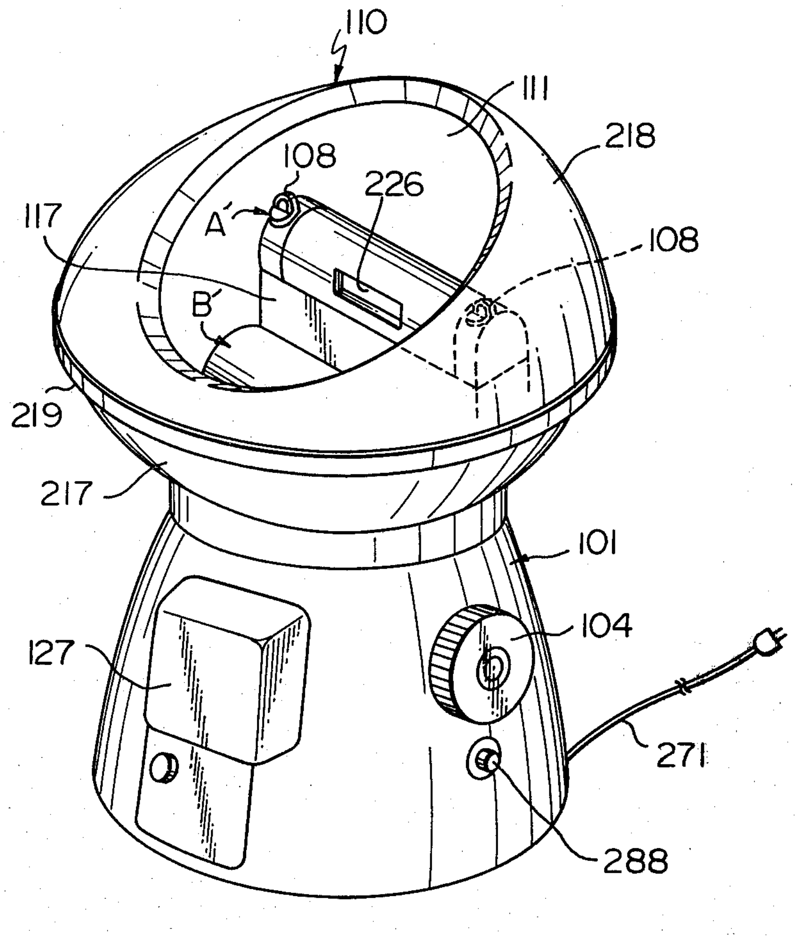
Figure 5:
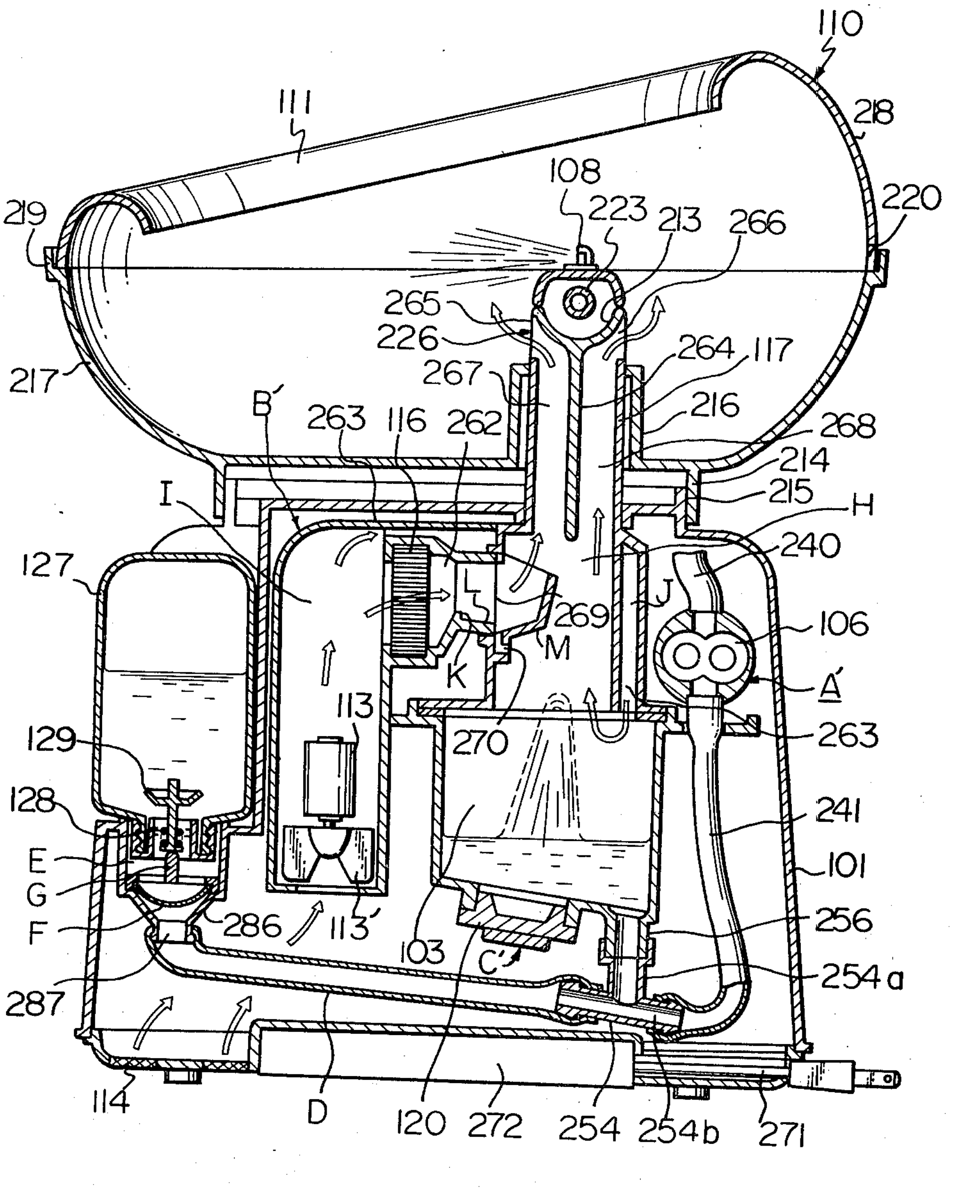

Now, with reference to FIGS. 4 and 5, the entire structure of the facial beauty device according to the second embodiment wherein various treatments intended in the present invention can be favorably attained shall be explained in the followings. Substantially the same as in the case of the first embodiment, this facial beauty device also comprises generally a body case 101 containing a water spraying means A′, heating means B′ and moistening means C′, and a hood 110 mounted on the case 101 and defining in front of the user's face the atmosphere for the respective facial beauty treatments generated by these means. In this embodiment, in particular, the water spraying means A′ is adapted to spray over the entirety of the user's face by rotating a plurality of water spraying nozzles so as to sequentially shift spraying direction with a later described arrangement. An operating handle 104 of the means A′ for rotating such spraying nozzles is rotatably fitted to a side wall of the body case 101. The hood 110 including a face resting opening 111 has the plane of the opening 111 inclined at a smaller angle with respect to the horizontal line than in the case of the first embodiment as illustrated so as to render the face resting easier, and the hood is closed at the bottom so as to watertightly pass, generally, only a delivery tube 117 having delivery ports for delivering into the hood a heated air stream generated by the heating means B′ and a mist produced by the moistening means C′, together with the plurality of rotatable water spraying nozzles described later. Thus, a nozzle base carrying the water spraying nozzles and having hot air stream and mist delivery ports is positioned as deflected to the side on which the forehead of the face rested against the opening 111 is to be positioned, that is, to the rear side of the device as seen from the user, from the center axis of the hold 110 so that, specifically, the water sprays jetted toward the face from the water spraying nozzles will not directly enter the nose holes of the user. The moistening water reservoir 103 is also disposed at a position below the delivery tube 117 as separated from a water feeding tank 127 which is removably fitted to the front side of the case 101. The water feeding tank 127 is connected to the reservoir 103 and water spraying means A′ in a manner later described.

Referring here briefly to a water feeding arrangement from the water feeding tank 127 to the reservoir 103 and water spraying means A′, water in the water feeding tank 127 is fed to the reservoir 103 and spraying means A′, as seen in FIG. 5, through a water feeding pipe D connected between a lower opening 287 of a receiving port E provided in the form of a recess on the front side of the body case 101 for the tank 127 and one end of a horizontal pipe **254*b* of a T-joint 254 connected to the respective water feeding ends of the reservoir 103 and water spraying means A′. In this case, vertical pipe 254A of the T-joint 254 is connected as directed upward to the opening end of a tube part 256 provided as directed downward in the lowermost part of the reservoir 103 inclined at its bottom toward rear side from the front side of the case 101 and the water feeding pipe D and lateral pipe 254*b* are preferably also inclined similarly to the bottom of the reservoir 3 so that the other end of the lateral pipe 254*b* connected to the lower opening end of a water feeding pipe 241 of the water spraying means A′ will be downstream with respect to the opening 287 of the tank receiving port E as well as an end of the lateral pipe 254*b*** connected to the feeding pipe D.

Figure 6:
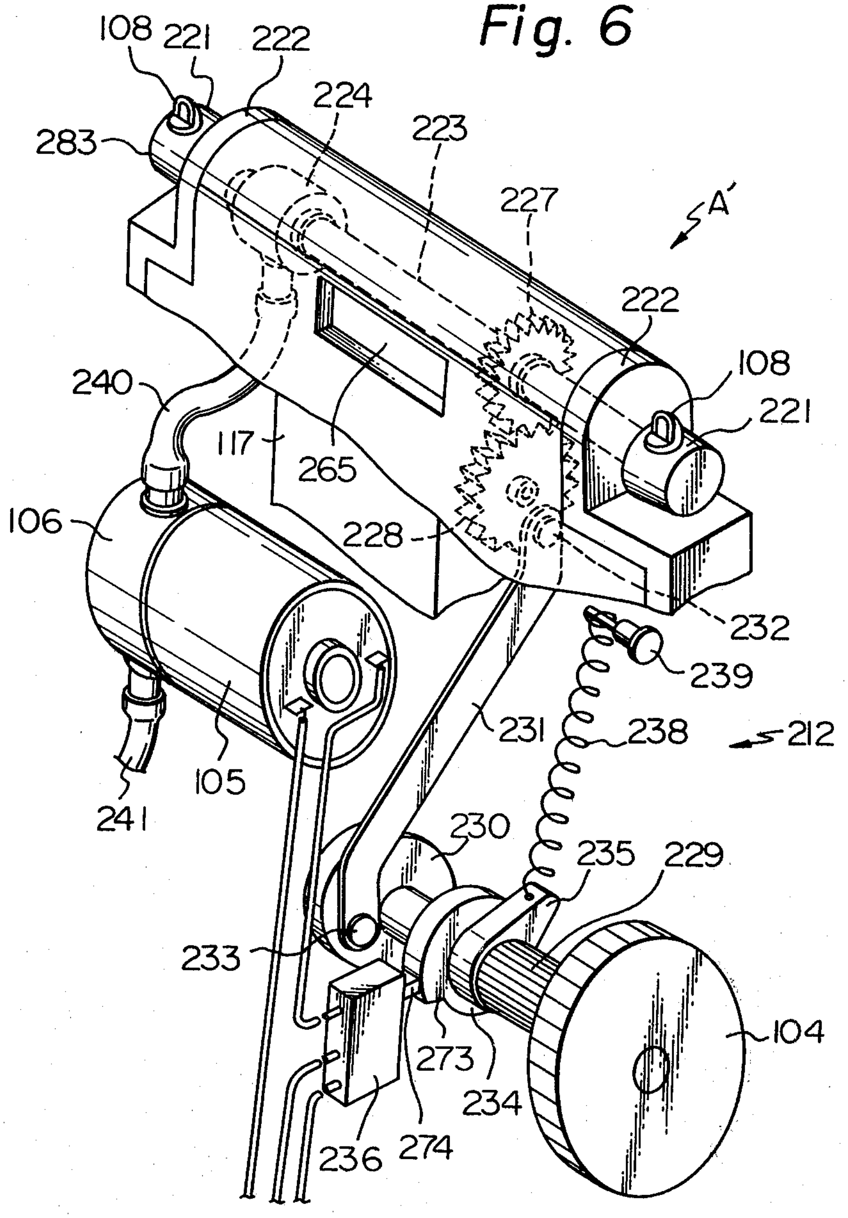
FIG. 6 is a fragmentary perspective view showing in a magnified scale a water spraying means for cooling and washing facial skin and its associated operating mechanism used in the second embodiment shown in FIGS. 4 and 5.
Figure 7:
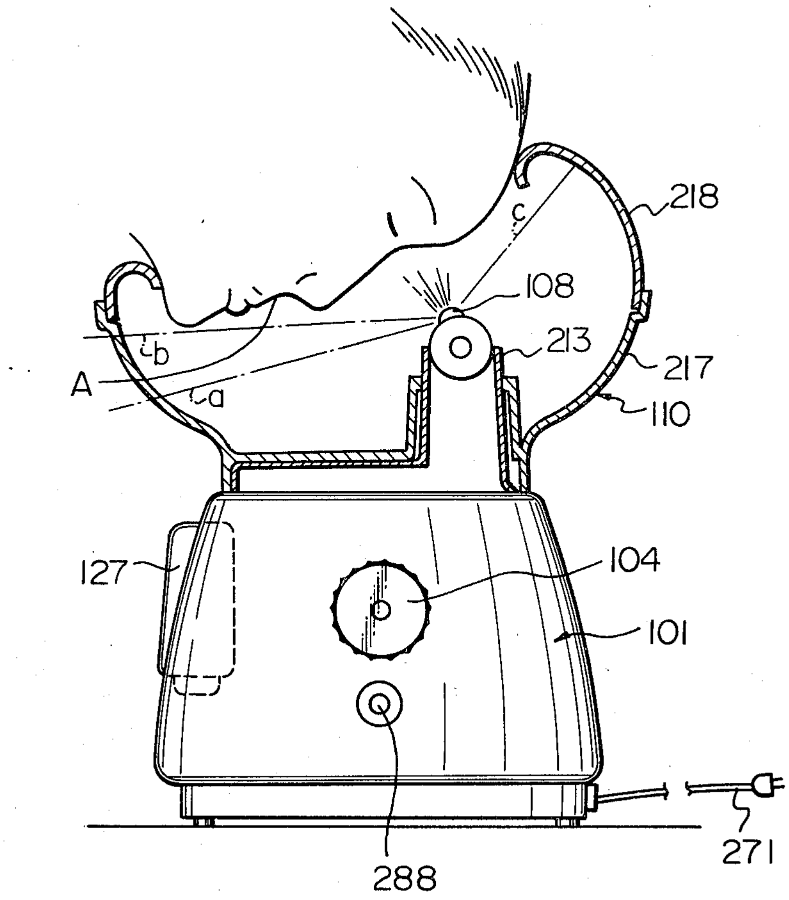
FIGS. 7 and 8 show a preferred water spray diffusing range in the facial beauty device of the second embodiment and are respectively partly sectioned side and front views in use.

Now, the arrangement of the water spraying means A′ of this embodiment shall be described with reference to FIGS. 5 and 6. The particular means A′ comprises generally a motor 105, a pump 106 driven by the motor, a nozzle base 213 provided on a projected end of the delivery tube 117 which is mounted on the reservoir 103 so as to project from the upper opening of the reservoir 103 substantially to the center of the inside space of the hood 110 through the bottom of the hood and to extend substantially in transversing direction with respect to the vertical direction of the user's face rested against the hood, the nozzle base 213 extending also in the same transversing direction of the tube 117, a pair of nozzle members 108 provided rotatably at both ends in the transversing extended direction of the nozzle base 213, a connecting pipe 223 supported axially rotatably between rocking bearings 222 provided at the both extended ends of the nozzle base 213 and connecting between the both nozzle members 108, and a spray rocking mechanism 212 operated by the before described water spray operating handle 104 so as to axially rotate the connecting pipe 223 with the nozzle members 108.

The before described water feeding pipe 241 is connected at the upper end to a suction port of the pump 106 and a delivery port of the pump is connected to the connecting pipe 223 through a delivery pipe 240 and a rockable pipe-joint 224 provided on the periphery of a water feeding port of the connecting pipe 223. Each of the nozzle members 108 is fitted through a nozzle holder 221 to each end of the connecting pipe 223 extending in the before described transversing direction from each of a pair of rocking bearings 222 and is integrally locked with the holder 221 by a cap 285, in a manner later detailed with respect to FIG. 15. As the nozzle members 108 are so fitted to the holder 221 that axial water path of the respective nozzle members 108 intersects substantially at right angles the longitudinal direction of the holder 221 and pipe 223, water fed by the pump 106 will be jetted substantially at right angles with respect to the extending direction of the nozzle base 213, that is, toward the hood opening 111 against which the face is rested. In the present instance, however, in contrast to the first embodiment, the respective nozzle members 108 have a water colliding wall outside water jetting port so that the jetted water will collide with this colliding wall to further change the direction and will be sprayed locally against the user's face in a diffusion pattern determined by a surface shape of the colliding wall but, as the spray rocking mechanism 212 axially rotates the nozzle holder 21 and connecting pipe 223 in a manner described later, the water spray will be caused to be blown against the entire face while being moved between the forehead and the jaw of the face.

Each of the nozzle members 108 is made, as shown in FIGS. 15A to 15C, substantially to be cylindrical and provided at one end with a lateral groove **108*a* transversing at right angles the longitudinal direction of the member and along the axial line with a water path 108***b* of a small diameter communicating between the groove 108*a* and the other end adjacent which the water path 108*b* is made to have a further reduced diameter to provide at the other end a nozzle 108*b*'. In front of the nozzle 108*b*' in the longitudinal direction of the member 108, the jetted water colliding wall 108*c* formed by a projected end from the other end of the member 108 is provided and its jetted water colliding surface is inclined with respect to the longitudinal direction of the member so that the water will be diffused substantially in the lateral direction with respect to the longitudinal direction. An engaging ring groove 108*d* is provided adjacent the nozzle end on the peripheral surface of the cylindrical member 108 and an annular elastic sealing member 108*e* is fitted in another peripheral groove made adjacent the center. On the other hand, each of the nozzle holders 221 respectively fitted to each end of the connecting pipe 223 mounted on the nozzle base 213, aligning their water passages 223*a* and 221*a* with each other, is provided with a nozzle receiving port 280 defined by a nozzle receiving part 281 box-shaped in the illustrated case and projected out of each longitudinal end of the holder 221, and this nozzle receiving hole 280 is communicated with the water passage 221*a* of the holder 221 and opened in the direction intersecting substantially at right angles the passage 221*a*. The nozzle member 108 is housed at the end of the groove 108*a* in the receiving hole 280, as inserted therein in a direction shown by an arrow d in FIG. 15A, and the sealing member 108*e* closely seals a gap between the member 108 and the hole 280. In this portion, the nozzle 108*b*' communicates substantially rectangularly with the water passage 221*a* of the holder 221 and the nozzle member 108 is locked to the holder by a cap 283 fitted to the longitudinal end of the holder to cover its box-shaped extension 281, in the longitudinal direction shown by an arrow e in FIG. 15A. This locking is attained by a fitting engagement of a flange 283*b* provided along the opened end edge of the cap 283 into a groove provided on the holder end side of the receiving part 281 of the holdr 221 and also a fitting engagement of side edges of a nozzle receiving slot 283*a* made in the cap by cutting partly off the opening end edge of the cap 283 into the engaging groove 108*d* of the nozzle member 108. Accordingly, the cap 283 fitted in the direction e intersecting at right angles the nozzle member inserting direction d is capable of effectively presenting the nozzle member 108 from being caused to escape in the direction d due to the water pressure exerted to the member.

Figure 13A:
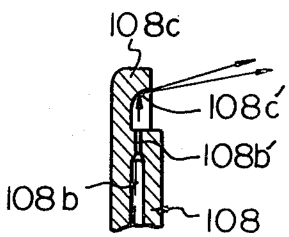
Figure 13B:
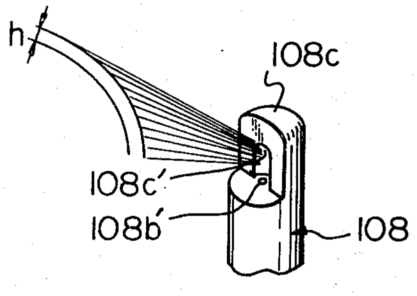

The diffusion of the water spray in this embodiment should preferably be made in a pattern having a zone expanding long in the extending direction of the nozzle base, that is, in the width direction of the face of the user as will be later described further. This spray diffusion pattern is determined by the shape of the colliding wall surface of the nozzle member 108, and FIGS. 13A and 13B show an example thereof. In this case, a colliding surface 108*c*' of the colliding wall 108*c* is made substantially spherical so that the diffused spray pattern wall be an arc having a width h as in FIG. 13B. Further, FIGS. 14A and 14B show another example in which a colliding surface 108*c*" is flat so that the spray pattern will be linear narrow long as in FIG. 14B.

Referring back to FIG. 6, the spray rocking mechanism 212 comprises a driven side rocking gear 227 fixed on the peripheral surface of the connecting pipe 223 preferably adjacent the holder 221 at one end of the pipe 223, a driving side rocking gear 228 meshing with the gear 227 and borne, for example, outside the delivery tube 117, and a rocking link 231 connected by means of respective link pins 232 and 233 between the disk body of the gear 228 and a rocking lever 230 fitted to the inner end of a shaft 229 bearing the water spray operating handle 104 in the body case 101. In the illustrated case, the shaft 229 is further provided with a switch operating cam 234 and a return lever 235, a lobe 273 of the cam 234 is made to contact a push button 274 of a microswitch 236 inserted between an electric current source and the motor 105, and a return spring 238 engaged at one end with a pin 239 provided at a proper stationary position in the device is engaged at the other end with the projecting end of the lever 235 so that the shaft 229 as well as the nozzle members 108 connected to the shaft through the respective members referred to will be normally biased in a predetermined return position. It is convenient that positional relation between the cam 234 and the lever 235 is such that, in the return position of the lever 235 as biased by the spring 238, the lobe 273 of the cam 234 urges the push botton 274 of the switch 236 into its retracted position of switching off the switch contacts connected to the motor 105 and, with a rotation of the handle 104 and lever 235 against the return spring, the cam 234 allows the push button 274 to shift to its projecting position of switching on the switch.

Referring now to the structure of the heating means B' with reference to FIG. 5, the means comprises a hot air stream passage 262 communicating from a lateral side with a vertical passage H defined by the lower part of the delivery tube 117 which is upright from the upper opening of the reservoir 103 through a hot air stream delivery port 269 provided in a side wall of the vertical passage H, substantially the same type porous plate heater 116 as in the first embodiment fitted across an inlet port of the hot air stream passage 262, and a suction passage I communicating at one end with the inlet port of the passage 262 and having an air inlet at the other end which is, in the illustrated case, hung vertically from the inlet port of the passage 262, and an air blowing means having a motor 113 provided within the passage I and a fan 113' fitted to the rotary shaft of the motor for producing an upward air stream. In this case, the body case 101 has an air suction port 114 provided with an antidust filter in the bottom wall of the case 101, so that the air flow sucked in through the suction port 114 with the rotation of the fan 113' will be heated while passing through the heater 116 from the suction passage I and the heated air stream will be delivered into the vertical passage H through the hot air stream passage 262.

On the other hand, on the periphery of the hot air stream passage 262, there is provided a cool air stream passage 263 communicating at one end with the suction passage I and at the other end with the upper space in the reservoir 103 on the side of a flow passage J enclosing the outer periphery of the vertical passage H so that a part of the air flow in the suction passage I will be fed into the reservoir 103 through the flow passage J from this cool air stream passage 263. The cool air stream fed from the passage J into the space within the reservoir 3 opened only at the lower end of the vertical passage H will therefore produce air flow flowing upward through the passage H and the hot air stream from the hot air stream passage 262 will rise together with this upward cold air stream through the passage H. The delivery tube 117 continuing upstream the vertical passage H is formed rectangular in the cross-section as seen in FIG. 6, while the nozzle base 213 is disposed at the upper end of this rectangular tube 117, elongated delivery ports 265 and 266 opening on the front and rear sides of the nozzle base are provided adjacent the nozzle base to extend in the extending direction of the nozzle base substantially as intermediate position between both side walls on the long sides of the rectangular tube 117, that is, between the respective the nozzle members 108, so that the hot and cool air streams rising from the passage H will be delivered into the hood through these delivery ports 265 and 266 of the delivery tube 117.

According to this embodiment, as a preferable aspect of the present invention, a partition plate 264 is provided in the delivery tube 117 so as to be extended in the lengthwise direction of the rectangular tube 117 and suspended from the lower surface of the nozzle base 213 down to a position adjacent the delivery port 269 of the hot air stream passage 262, and the tube 117 is separated by this plate 264 into front and rear flow passages 267 and 268 respectively continuous to the delivery ports 265 and 266 of the delivery tube 117 from the vertical passage H. Further, a frame M guiding upward the hot air stream from the delivery port 269 is fitted to the lower end edge of the delivery port 269 so as to extend at the tip substantially to the center of the vertical passage H, so that the hot air stream from the delivery port 269 will be guided mostly into the separated flow passage 267 and will be delivered out of the delivery port 265 on the front side of the delivery tube 117 and, on the other hand, the cool air stream rising through the vertical passage H from the space within the reservoir 103 from the cool air stream passage 263 will be guided mostly into the other separated flow passage 268 and will be delivered out of the delivery port 266 on the rear side.

The moistening means C′ of this embodiment comprises the reservoir 103 inclined in the bottom as before described and the ultrasonic oscllator 120 water-tightly fitted to the inclined bottom of the reservoir with the ultrasonic radiating side disposed upward for communicating with water within the reservoir. The ultrasonic oscillator 120 is preferably connected to the before described microswitch 236 inserted between the motor 105 of the water spraying means A′ and the current source so that, simultaneously with the operation of switching on the switch 236 by the rotation of the spray operating handle 104, the electric power will be fed to the oscillator 120. Simultaneously with the oscillation of the oscillator 120, water in the reservoir 103 is oscillated by the generated ultrasound and a mist of fine water droplets is jetted up into the upper space of the reservoir. This mist thus jetted up will be carried to the respective flow passages 267 and 268 of the delivery tube 117 by the cool air stream rising into the vertical passage H through the flow passage J from the cool air stream passage 263. At this time, the fine water droplets carried only by the cool air stream into the separated flow passage 268 is delivered as a readily visible white mist out of the delivery port 266 into the hood, so that the user can confirm that the interior of the hood is being moistened. On the other hand, the fine water droplets carried partly into the other flow passage 267 is heated by the hot air stream from the passage 262 and an air stream which is moistened to a certain extent at a high temperature is delivered out of the delivery port 265 into the hood. These white misty stream relatively of a higher moisture and lower temperature and stream relatively of a lower moisture and higher temperature are caused to be mixed together within the hood 110 while circulating along the peripheral wall of the hood after being delivered out of the respective laterally opened ports 225 and 226 and, within the hood, a still visibly white atmosphere of optimum temperature and moisture for warming the user's face is produced.

A part of the heated fine water droplets rising through the separated flow passage 267 are likeely to be dewed when they contact the separating plate 264 and side walls of the delivery tube 117 and to be deposited on their surfaces, and thus deposited hot water drops will flow down along the separating plate 264 and side walls but will be caught within the upward opened guiding frame M so as to be prevented from dropping into the reservoir 103. The ultrasonic oscillator 120 provided on the inclined bottom surface of the reservoir 103 as described before is fitted so as to direct its center of ultrasonic radiating direction substantially toward the lower end of the separated flow passage 268 for the cool air stream, so that the fine water droplets jetted up in the passage H are prevented from directly hitting the heated frame M and dropping into the reservoir 103 after being heated by the frame. These preventions of the heated water droplets from dropping into the reservoir 103 prevent possible deterioration in cooling ability of water in the reservoir for the oscillator 120 due to the rise of water temperature and maintain a desired mist generating efficiency. The hot water caught by the frame M as is not capable of reaching the heater 116, since the bottom surface L of the heated air stream passage 262 is made higher than the lower edge of the delivery port 269 at a partition rib K provided adjacent the heater 116 and the bottom surface L is inclined toward the lower edge, and rather drop into the reservoir 103 through a draining hole 270 provided at the lower edge of the frame M. However, this hot water will be further heated to be partly evaporated by the hot air stream while flowing along the inside surace of the frame M or the inclined bottom surface L, so that the hot water dropping into the reservoir will be kept minimum. Any dropping hot water is directed to a side part of the reservoir, so that it does not hit the rising mist nor render the mist generating efficiency deteriorated.

Reasons for defining the respective hot air stream flow passage 265 and cool white mist flow passage 266 with the partition plate 264 is that, in case all the fine water droplets jetted up from the reservoir are heated by the heated air stream from the passage 226, the hot water fine droplets are first dewed to be a white mist only when they are delivered into the hood but this white mist will disappear in a comparatively short time so as to render the generated atmosphere highly moistened at a high temperature to be hard to recognize, and it is advantageous to generate in the flow passage 266 such cool white mist which can well keep the white misty state within the hood, and that, if all the fine water droplets are heated, the amount of the deposited hot water dewed in contact with the inside surfaces of the delivery tube 117 will increase and the amount of the hot water dropping into the reservoir 103 will increase while the amount of the generated mist will decrease and, in order to compensate for such decrease, capacities of the oscillator and reservoir must be made larger. The partition plate 264 is advantageous to solve these problems.

Now, the operation of the facial beauty device of the second embodiment having the above described arrangements shall be referred to mostly with reference to FIGS. 7 to 12. In this embodiment, as has been referred to, the motor 105 of the water spraying means A′ is connected to the microswitch 236 made ON and OFF by the rotation of the operating handle 104 and its switch cam 234 so that the cooling and washin actions by means of the water spray and the rocking operation of the spray nozzle members can be achieved by the rotation of the single operating handle 104, whereas the motor 113 and heater 116 of the heating means B′ as well as the oscillator 120 of the moistening means C′ are respectively separately operated by actuations of different switches (not shown). A current source cord 271 connecting an electric current in the device and comprising these electric elements to an alternating current source is normally wound on a cord reel 272 provided on the bottom surface of the body case 101 as seen in FIG. 5. When the user first removes the water feeding tank 127 from the case 101, pours water into the tank to fill it, inserts the water feeding port of the tank into the tank receiving port E of the case to fit the tank 127 to the case 101, the plug 129 normally closing the water feeding port of the tank with the spring pressure will open the port and water will be fed into the reservoir 103 and up to the suction port of the pump 106 by the before described water feeding arrangement. When the current souce cord 271 is connected and the switches for actuating respectively the motor 113, heater 116 and oscillator 120 are turned ON, the heating means B′ and moistening means C′ are actuated and the hot and highly moistened atmosphere is produced inside the hood 110 in the manner as described above. In this state, the user rests her face against the opening 111 of the hood to warm the face and, when the warming and moistening of the face is sufficiently made, the switches are turned OFF. Then, the operating handle 104 normally biased by the spring 234 into the OFF position seen in FIGS. 6 and 11A is slightly rotated clockwise in FIG. 7 or 11A against the return biasing, the push button 274 keeping the microswitch 236 in the normally closed contact position with the lobe 273 of the switch cam 234 is removed from the cam lobe 273 to project so as to attain the state shown in FIG. 11B, the motors 105 is actuated, whereby the water spraying means A′ is operated and the water spray is jetted out of the nozzle members 108. By this rotation of the handle 104 and switch cam 234, the nozzle members 108 are rotated to the position shown in FIG. 11B through the above described rocking mechanism but, in this position of the nozzle members 108, the water spray is jetted in the direction shown by the chain line a in FIG. 7 but not be jetted out of the hood opening 111. When the handle 104 is rotated further clockwise, the nozzle members 108 are also rotated, the jetted water spray will come in the direction of the chain line b in FIG. 7 and the cooling and washing are started first from the jaw side. When the handle 104 is further rotated to the maximum rotating position of the state of FIG. 11C in which the jetting direction is indicated by the chain line c in FIG. 7 and the maximum rotation of the handle 104 is defined by a proper stopper, the face can be cooled and washed by the water spray sequentially from the jaw over to the forehand. If the handle 104 is repeatedly rotated as desired, the face can be well cooled and washed.

Figure 8:
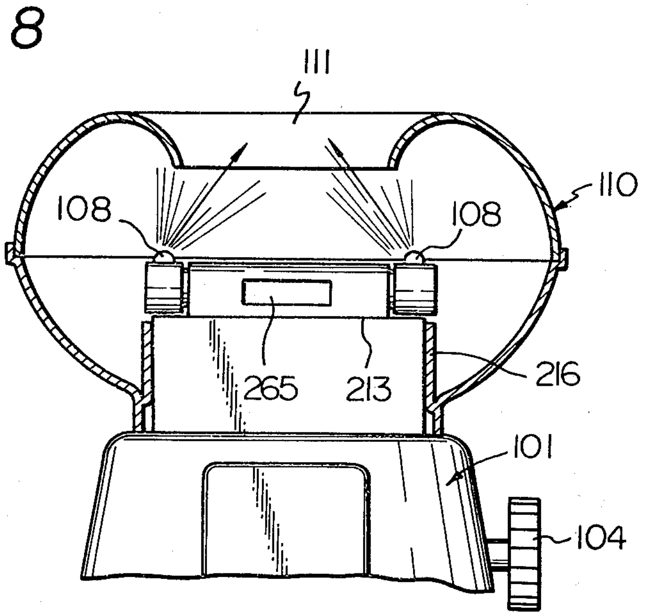

In this case, it is preferable that the hood opening 111 is elliptic so as to be fittable to the user's face and the spray nozzle members 108 are so mounted as to incline the spray center from each end of the nozzle base 213 toward the major axis of the elliptic opening as shown in FIG. 8 so that the sprays jetted out of the pair of nozzle members 108 will substantially uniformly hit the face along the major axis of the opening, or such colliding wall in front of the water jetting port as has been described is so designed to achieve such spraying mode as above.

Figure 12:
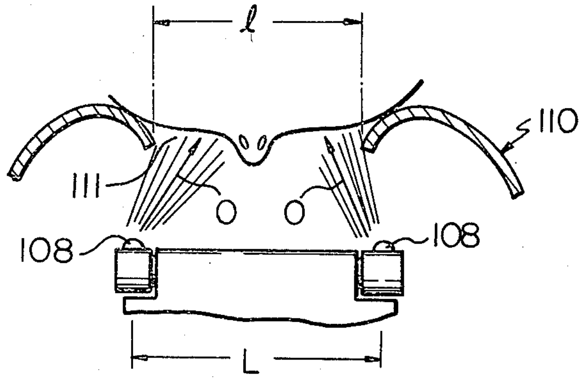
FIG. 12 is an explanatory view for showing the relation of the hood opening width to the distance between a pair of water spraying nozzles in the facial beauty device of the second embodiment.

The relative spray directions of the both nozzle members 108 shall be detailed with reference to FIG. 12. First, the distance L between the respective nozzle members 108 at both ends of the nozzle base 213 is made larger than the minor axis "1" of the elliptic hood opening 111 and, therefore, the spray center lines "0" from both nozzles are inclined toward each other so that the distance between them on the user's face will be smaller than the minor axis "1". Such relation between the spray direction and the hood opening width achieves that the spray will not be discharged outward through any gap between the face rested against the hood opening and the peripheral edge of the opening, the spray will hit the face substantially at right angles with respect to both sides of the face to elevate the washing ability, and at the same time a massaging effect of the spray can be additionally elevated since the spray is performed substantially under the maximum pressure.

Figure 9:
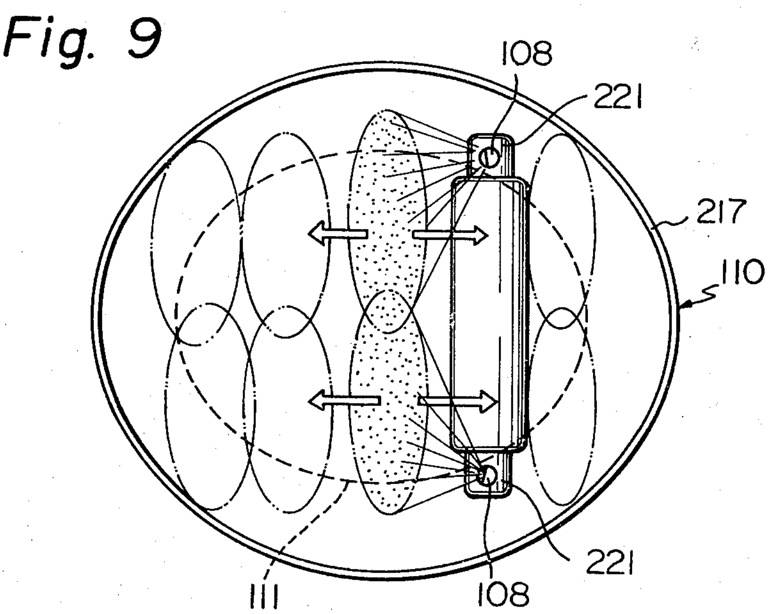

Further, as shown in FIGS. 9 and 10, the spray pattern from each nozzle member 108 is made to be a so-called flat spray pattern in which, as seen in FIG. 10, each spray zone is long in the width direction of the face, that is, in the minor axis direction of the elliptic hood opening 111 but is short in the vertical or major axis direction of the face. It is preferable to obtain a combined pattern in which these flat patterns extend to be narrow long over the width of the face as seen in FIG. 8. Therefore, the fact that the face can be cooled and washed sequentially as described above by the spray of such band-shaped composite pattern as is obtained by the pair of spray nozzles which are separated from each other in the width direction of the face and extends in the width direction of the face, in advantageous in that, not only the above described direct spray jetting into the nose holes by the position of the nozzle deflected to the forehead size will be avoided, but also the time of jetting to the nose can be reduced, so that any difficulty in breathing during the use will be reduced, unpleasant feeling likely to be incurred in the case of the direct and long spraying to the parts of eye and nose from the first to the end will be eliminated by the gradually moving spray, and the facial beauty treatment can be performed in a calm state of the user, and, when the spraying to the eye and nose parts for a long time is not desirable to the user, the unpleasantness can be miminized by quickly rotating the handle 104 in such part. Further, with the band-shaped composite patterned spray, substantially uniform spraying can be obtained with a smaller amount of water, the consumption of water will be minimized and the content of water in the device can be also minimized.

While in this embodiment it is shown to use a pair of spray nozzles, it is possible to employ more three nozzles properly arranged at intervals smaller than in the case of a pair on the nozzle base, in which event a plurality of spray directions from these nozzles will be substantially rectangular to the face substantially elliptic in section and the sprays can efficiently hit the face and, even if the pump or motor of the water spraying means is of a comparatively small capacity, a sufficient spraying effect can be obtained.

When the face washing by such water spraying as above is finished, the user releases the rotating handle, then the handle 104 and the nozzle members 108 connected to the handle through the switch cam 234 and rocking mechanism 212 return respectively automatically to the original positions shown in FIG. 11A due to the biasing of the return spring 238, and the switch 236 interrupts the current feed to the motor 105 driving the pump 106 to stop the operation of the spraying means A'.

Water sprayed in the hood accumulates in the bottom of the hood 110. The before described water-tightness between the bottom of the hood 110 and the delivery tube 117 passing therethrough is advantageously attained, as seen in FIG. 5, by a tubular projection 216 made in the bottom of the hood 110 for partly enclosing the delivery tube 117, as projected from the bottom substantially in coincidence with the cross-sectional contour of the delivery tube at least to the lower edges of the delivery ports 265 and 266 on the periphery of the delivery tube through the bottom of the hood. While the hood 110 is thus given a capacity of containing sufficient water used by this projection 216, the delivery tube 117 and projection 216 are in sliding contact with each other, so that the hood 110 will be easy to fit to and remove from the body case 101 and the accumulated used water can be advantageously thrown away, and the once removed hood can be easily fitted again to the case 101 as properly stably positioned since the delivery tube 117 and projection 216 respectively having elongated cross-sectional contours mating with each other will unrotatably engage with each other. Further, as shown in FIG. 5, the hood 110 of this embodiment is formed of a bottom side half 217 including the projection 216 and an upper side half 218 including the opening 111. The upper side half 218 is housed along its lower end edge within a flange 219 provided along the upper end edge of the bottom side half 217 to be mounted on the half 217. Therefore, in throwing away the accumulated used water, the upper side half 218 is first removed and the water can be easily removed only with the bottom side half 217 containing the water in the bottom. In the illustrated case, further, a ventilating hole 220 is provided, for example, in a part of the lower edge of the upper side half 218 in the form of a cut, so that, even if the user considerably strongly contacts the face with the opening 111 in using the device, the breathing will not be felt to be difficult.

When unused water remains in the reservoir 103 which is provided as fixed inside the body case 101 in order to render the manufacture easy or the arrangement simple, in the case of the present embodiment, a draining push button 288 provided in the case 101 adjacent the operating handle 104 should be pushed. As shown in FIG. 16, this push button 288 is connected in parallel with a pair of fixed contacts of the microswitch 236 inserted between the motor 105 and the current source so that no current will be normally passed between the contacts of the microswitch 236 which are normally closed by the switch cam 234 while the device is not operated. Therefore, when the push button 288 is pushed in such state of the microswitch 236, a current is fed to the motor 105 irrespective of the spray rocking mechanism 212 and the pump 106 is thereby operated to drain the water in the reservoir into the bottom side half 217 of the hood through the nozzle members 218. While the remained water can be of course drained by the rotation of the operating handle 104, the nozzle members 108 are to be also rotated in this case through the rocking mechanism 212 so that the handle 104 may happen to be rotated excessively to a position of causing the sprays to be jetted toward the opening 111. When the draining push button 288 which can operate the water spraying means without requiring the rotation of the handle 104 as referred to above is used, the remained water in the reservoir can be continuously drained while the nozzle members jet sprays toward the hood bottom surface.

Since the bottom of the reservoir 103 is inclined and water is drained by the water spraying means A' through the tube part 256 provided in the lowermost position of the bottom of the reservoir, as has been described, no water will remain in the reservoir when the draining by the push button 288 is performed. With the fall of the water level without the reservoir 103, water in the feeding tank 127 will be also drained to be sent simultaneously to the lower end of the water feeding pipe 241 through the water feeding pipe D and the lateral pipe **254*b* of the T-joint 254 respectively inclined toward the lower end of the water feeding pipe 241 connected to the pump 106 and will be drained together with the remained water in the reservoir 103, so that the reservoir 103, water feeding tank 127** and connecting part between them can be drained substantially perfectly.

Here, the structure for automatically feeding or draining water to or from the water feeding tank 127 advantageously employed as combined with the entire structure and its operation of this embodiment shall be described particularly with reference to FIG. 18. A double layer cap 275 defining in the inner tube part a water passing port 277 and having in the center a plug 129 normally biased outward of the tank by a spring 128 to close the water passing port 277 is screwed at an outer tube part of the cap to a tubular opening 127' of the water feeding tank 127 through an elastic seal 276 so as to close the opening 127'. The plug 129 is slidably supported within a central ring 278 of a supporting arm 279 transversely provided in the inner tube part and the spring 128 is held between the outer end flange of the plug 129 and the ring 278. The tank receiving port E provided in the body case 101 as described before is suspended from the case as a tubular body of a diameter sufficient to leave a space around the double layer cap 275 of the tank. The water feeding port 287 connected to the water feeding pipe D as described before is provided at an end of a conically constricted bottom part of the tubular port E. An inward protruding step part is provided preferably at the lower end of the tubular port E, and an annular filter supporting member 290 having an outer diameter fitting this step part and protruding, for example, a hemispherical filter F fixed at its peripheral edge in an inward opened groove of the member 290 is removably fitted on this step part. Further, in the center of the supporting member 290, there is provided a push rod G made integral with the member through a bridge part and projecting upward, that is, toward the opening of the receiving port E. A plurality of spaced projections 293 are provided outside the opening of the receiving port E so that, when the water feeding tank 127 is mounted on the projections 293 with its opening closed by the cap 275 inserted into the receiving port E, a gap 294 communicating the space within the receiving port E with the exterior air is left between the tank 127 and case 101. The plug 129 closing the water passing port 277 of the cap 275 of the thus mounted tak will collide with the push rod G of the filter supporting member 290 projecting into the receiving port E at the projecting end and will be pushed into the tank against the spring 128, the water passing port 277 will open and the reserved water within the tank will flow down toward the filter F. Therefore, any obstacles present within the water feeding tank or entering through the gap 294 will be filtered by the filter F. On the other hand, with the fall of water, air will rise into the tank through the gap 294 and the space within the receiving port E and, therefore, water will be smoothly fed from the tank. The filter can be easily taken out by gripping the push rod G and is therefore easy to clean. In case the filter is removed and is then forgotten to be again fitted and even the water feeding tank 127 is fitted, water will not be fed as there is no push rod G and obstacles still can be prevented from mixing in. It will be understood that this is important in such device wherein water in the water feeding tank and reservoir can be completely drained or, in other words, can be completely used as in this embodiment and also in preventing the failure of the device in using water sprays by nozzles.

While in the above described second embodiment it has been referred to that there is adopted the arrangement wherein the respective water spraying, heating and moistening means are respectively actuated by separate ON and OFF operations of the switch actuated by the handle rotated and the ones for the heater, motor and oscillator, these means may of course be operated respectively sequentially or selectively by any proper control means in the order of the heating and concurrent moistening, water spraying and finally heated-air blowing actions. For example, when the respective means are to be sequentially operated in response to the rotation of the operating handle, it will be preferable to combine the respective operations of these means and control means with the rotation of the operating handle so as to first operate the heating and moistening means, then to stop these means, thereafter to operate only the water spraying means as has been described and finally again to operate only the heating means.

According to the present invention, there is provided a facial beauty device wherein, as has been described above, the facial sauna effect is attained by producing the high temperature atmosphere which is highly moistened in the hood by using the means for generating the mist by oscillating water as it is, that is, at its own low temperature instead of using the steam generating autoclave used generally for the conventional facial sauna and combining with it the means for generating an air stream heated by electrically generated heat and, further, respective effects of cooling and washing the user's face to which the facial sauna effect is given by the means for applying low temperature water sprays against the face and further massaging the face under the water spray pressure can be given, so that there are effects but the facial beauty effect is elevated to be far higher than by the conventional facial beauty devices, and that the device is safe and easy to use. There can be provided a facial beauty device wherein the mist heated in the present invention will not be jetted into the hood under such a high pressure as the conventionally used steam, and neither anxiety nor unpleasantness will be given to the user in the case of using it. In one aspect of the present invention, further, the band-shaped spray patterns expanding in the width direction of the user's face can be moved so as to prevent water sprays from being blown directly into the nose holes and to thereby effectively prevent the user's anxiety and unpleasantness from being caused by the sprays during the use. In addition to these effects, such effects and advantages as disclosed with reference to the respective components of the device according to the present invention are rendering the facial beauty device of the present invention extremely useful in the practical use.

What is claimed is:

1. A facial beauty device including a body case, a hood mounted on said case and having an opening for resting thereagainst the user's face, and means for generating within said hood a heated and moistened atmosphere from water in a reservoir housed in the case; the device further comprising a passage communicating the upper space in said reservoir with the inner space of the hood and a water spraying means including a pump and nozzle housed within the case and spraying water in the reservoir substantially toward said opening of the hood, and said atmosphere generating means comprising means provided in the bottom of the reservoir for generating a mist within said passage by oscillating water in the reservoir, means for generating a moistened air stream directed toward the inner space of the hood through the passage together with said mist, and means for heating at least a part of said moistened air stream.

2. A device according to claim 1 wherein said mist generating means is an ultrasonic oscillator provided in the bottom of said reservoir at a position substantially corresponding to the lower end of said passage.

3. A device according to claim 1 wherein said nozzle of said water spraying means sprays water against a part of the user's face and is rockable for varying spraying direction so as to spray water over the entire area of the face.

4. A device according to claim 3 wherein said water spraying means initiates and terminates its water spray at a state where said spraying direction of said rockable nozzle is not directed toward said opening of said hood.

5. A device according to claim 1 wherein said nozzle of said water spraying means sprays water in a zone elongated in the width direction of the user's face and is supported rockably for shifting said elongated spray zone to spray water over the entire area of the face.

6. A device according to claim 5 wherein said elongated spray zone is formed by a plurality of said nozzles disposed along said width direction.

7. A device according to claim 6 wherein at least two of said plurality of nozzles disposed at both ends in said width direction have their spraying center directed substantially toward the center of said opening of said hood.

8. A device according to claim 1 wherein said opening of said hood is made on a plane inclined to be higher on the side of the forehead of the user's face and lower on the side of the jaw, and said nozzle is disposed at a deflected position on said higher side of said hood opening.

9. A device according to claim 5 wherein said elongated spray zone is formed by a plurality of said nozzles provided on a connecting water feed pipe extending in said width direction and supported axially rotatably.

10. A device according to claim 9 wherein said nozzles respectively comprise an elongated cylindrical nozzle member mounted to said feed pipe in a manner detachable in a direction perpendicular to the axis of the pipe, and said nozzle member is locked to its mounted position by means of a member fitted to the feed pipe in the axial direction of the pipe.

11. A device according to claim 10 wherein said nozzle members are respectively provided with a water jetting port opened in the longitudinal direction of the member and a colliding wall with which water jetted out of said jetting port collide to be dispersed in a lateral direction with respect to said longitudinal direction.

12. A device according to claim 9 wherein said connecting feed pipe is axially rotated by a rotation of an operating handle mounted rotatably to said case to rockably support said nozzles, and said pump of said water spraying means is actuated by a switch operated by said rotation of said operating handle.

13. A device according to claim 12 wherein said operating handle turns on and off said switch with a cam fixed on an axially rotatable shaft of the handle.

14. A device according to claim 1 wherein said air stream generating means comprises a hot air stream passage opened at one end in a side wall of said communicating passage and having at the other end said heating means, a cool air stream passage opened at one end in the upper part of said reservoir and also at the other end at a position substantially adjacent the heating means, and an air blowing passage which blows air toward respective said the other ends of said hot air stream passage and cool air stream passage.

15. A device according to claim 14 wherein said communicating passage is provided with a partition suspended from a delivery port of the passage opened inside said hood to a position adjacent said opened one end of said hot air stream passage, and said delivery port is divided by said partition into a first part deliverying into the hood an air stream of a relatively higher temperature and less moistened and a second part deliverying into the hood an air stream of a relatively lower temperature and more moistened.

16. A device according to claim 1 wherein said body case includes a water feeding tank removably fitted to the case for feeding water into said reservoir, said tank having a plug normally resiliently closing a water feeding port of the tank, and the body case is provided with a push rod for pushing said plug of the tank to open its said feeding port when the tank is fitted to the case and with a filter expanding in feeding direction of water from the tank.

17. A device according to claim 16 wherein said reservoir has a feed port opened downward at the bottom, said body case has a tank receiving port to a lower opening of which a feed pipe is connected, said feed pipe connects said tank receiving port through a T-joint to said feed port of the reservoir and a suction port of a pump of said water spraying means, and the feed pipe and a lateral pipe portion of said T-joint connecting between the feed pipe and the suction port of the pump are inclined to be lower in the water feeding direction.

18. A device according to claim 1 wherein said communicating passage has a non-circular shape in section and extends inside said hood, and said hood is provided at the bottom with a hollow cylindrical part having a shape in section intimately engageable to said sectional shape of the communicating passage and extending inside the hood to a position adjacent extended end of the passage so that the hood is detachably mounted at said cylindrical part to the passage.

* * * * *